000

United States Patent
Maile et al.

(10) Patent No.: US 7,559,901 B2
(45) Date of Patent: Jul. 14, 2009

(54) DETERMINING A PATIENT'S POSTURE FROM MECHANICAL VIBRATIONS OF THE HEART

(75) Inventors: Keith R. Maile, New Brighton, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 656 days.

(21) Appl. No.: 10/900,570

(22) Filed: Jul. 28, 2004

(65) Prior Publication Data
US 2006/0025699 A1 Feb. 2, 2006

(51) Int. Cl.
*A61B 5/02* (2006.01)
(52) U.S. Cl. ...................................... 600/528
(58) Field of Classification Search .................. 600/528; 607/17–19
See application file for complete search history.

(56) References Cited

U.S. PATENT DOCUMENTS

| | | | |
|---|---|---|---|
| 4,094,308 A | 6/1978 | Cormier | |
| 4,289,141 A | 9/1981 | Cormier | |
| 4,446,872 A | 5/1984 | Marsoner et al. | |
| 4,548,204 A | 10/1985 | Groch et al. | |
| 4,649,930 A | 3/1987 | Groch et al. | |
| 4,763,646 A | 8/1988 | Lekholm | |
| 4,777,960 A | 10/1988 | Berger et al. | |
| 4,830,006 A | 5/1989 | Haluska et al. | |
| 4,905,706 A | 3/1990 | Duff et al. | |
| 4,915,113 A | 4/1990 | Holman | |
| 4,989,611 A | 2/1991 | Zanetti et al. | |
| 5,097,831 A | 3/1992 | Lekholm | |
| 5,113,869 A | 5/1992 | Nappholz et al. | |
| 5,137,019 A | 8/1992 | Pederson et al. | |
| 5,159,932 A | 11/1992 | Zanetti et al. | |
| 5,179,947 A | 1/1993 | Meyerson et al. | |
| 5,205,283 A | 4/1993 | Olson | |
| 5,226,413 A | 7/1993 | Bennett et al. | |
| 5,305,745 A | 4/1994 | Zacouto | |
| 5,321,618 A | 6/1994 | Gessman | |

(Continued)

FOREIGN PATENT DOCUMENTS

EP  0474958  3/1992

(Continued)

OTHER PUBLICATIONS

Siejko, K. Z., et al., "Method for Correction of Posture Dependence on Heart Sounds", U.S. Appl. No. 11/037,275, filed Jan. 18, 2005, 26 pgs.

(Continued)

*Primary Examiner*—Mark W Bockelman
(74) *Attorney, Agent, or Firm*—Schwegman, Lundberg & Woessner, P.A.

(57) ABSTRACT

A system for determining a patient's posture by monitoring heart sounds. The system comprises an implantable medical device that includes a sensor operable to produce an electrical signal representative of heart sounds, a sensor interface circuit coupled to the sensor to produce a heart sound signal, and a controller circuit coupled to the sensor interface circuit. The heart sounds are associated with mechanical activity of a patient's heart and the controller circuit is operable to detect a posture of the patient from a heart sound signal.

20 Claims, 4 Drawing Sheets

U.S. PATENT DOCUMENTS

| | | |
|---|---|---|
| 5,391,190 A | 2/1995 | Pederson et al. |
| 5,411,531 A | 5/1995 | Hill et al. |
| 5,496,361 A | 3/1996 | Moberg et al. |
| 5,549,650 A | 8/1996 | Bornzin et al. |
| 5,549,654 A | 8/1996 | Powell |
| 5,554,177 A | 9/1996 | Kieval et al. |
| 5,593,431 A | 1/1997 | Sheldon |
| 5,628,777 A | 5/1997 | Moberg et al. |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,725,562 A | 3/1998 | Sheldon |
| 5,792,195 A | 8/1998 | Carlson et al. |
| 5,836,987 A | 11/1998 | Baumann et al. |
| 5,935,081 A | 8/1999 | Kadhiresan |
| 5,951,593 A | 9/1999 | Lu et al. |
| 5,991,661 A | 11/1999 | Park et al. |
| 6,044,297 A | 3/2000 | Sheldon et al. |
| 6,044,298 A | 3/2000 | Salo et al. |
| 6,044,299 A | 3/2000 | Nilsson |
| 6,048,319 A | 4/2000 | Hudgins et al. |
| 6,053,872 A | 4/2000 | Mohler |
| 6,058,329 A | 5/2000 | Salo et al. |
| 6,064,910 A | 5/2000 | Andersson et al. |
| 6,076,015 A | 6/2000 | Hartley et al. |
| 6,104,949 A | 8/2000 | Pitts Crick et al. |
| 6,115,630 A | 9/2000 | Stadler et al. |
| 6,144,880 A | 11/2000 | Ding et al. |
| 6,152,884 A | 11/2000 | Bjorgaas |
| 6,161,042 A | 12/2000 | Hartley et al. |
| 6,190,324 B1 | 2/2001 | Kieval et al. |
| 6,193,668 B1 | 2/2001 | Chassaing et al. |
| 6,208,900 B1 | 3/2001 | Ecker et al. |
| 6,208,901 B1 | 3/2001 | Hartung |
| 6,273,856 B1 | 8/2001 | Sun et al. |
| 6,275,727 B1 | 8/2001 | Hopper et al. |
| 6,280,409 B1 | 8/2001 | Stone et al. |
| 6,298,269 B1 | 10/2001 | Sweeney |
| 6,324,421 B1 | 11/2001 | Stadler et al. |
| 6,351,672 B1 | 2/2002 | Park et al. |
| 6,360,127 B1 | 3/2002 | Ding et al. |
| 6,366,811 B1 | 4/2002 | Carlson |
| 6,368,283 B1 | 4/2002 | Xu et al. |
| 6,381,493 B1 | 4/2002 | Stadler et al. |
| 6,397,100 B2 | 5/2002 | Stadler et al. |
| 6,415,033 B1 | 7/2002 | Halleck et al. |
| 6,440,082 B1 | 8/2002 | Joo et al. |
| 6,466,821 B1 | 10/2002 | Pianca et al. |
| 6,477,406 B1 | 11/2002 | Turcott |
| 6,478,746 B2 | 11/2002 | Chassaing et al. |
| 6,491,639 B1 | 12/2002 | Turcott |
| 6,520,924 B2 | 2/2003 | Lee |
| 6,522,923 B1 | 2/2003 | Turcott |
| 6,527,729 B1 | 3/2003 | Turcott |
| 6,567,700 B1 | 5/2003 | Turcott et al. |
| 6,575,916 B2 | 6/2003 | Halleck et al. |
| 6,625,493 B2 | 9/2003 | Kroll et al. |
| 6,626,842 B2 | 9/2003 | Oka |
| 6,643,548 B1 | 11/2003 | Mai et al. |
| 6,650,940 B1 | 11/2003 | Zhu et al. |
| 6,658,292 B2 | 12/2003 | Kroll et al. |
| 6,665,564 B2 | 12/2003 | Lincoln et al. |
| 6,719,701 B2 | 4/2004 | Lade |
| 6,795,732 B2 | 9/2004 | Stadler et al. |
| 6,804,558 B2 | 10/2004 | Haller et al. |
| 6,810,287 B2 | 10/2004 | Zhu et al. |
| 6,824,519 B2 | 11/2004 | Narimatsu et al. |
| 6,830,548 B2 | 12/2004 | Bonnet et al. |
| 6,845,263 B2 | 1/2005 | Kawaguchi |
| 6,913,577 B2 | 7/2005 | Bardy |
| 7,127,290 B2 | 10/2006 | Girouard et al. |
| 7,248,923 B2 | 7/2007 | Maile et al. |
| 2001/0012955 A1 | 8/2001 | Goedeke et al. |
| 2001/0047125 A1 | 11/2001 | Quy |
| 2002/0001390 A1 | 1/2002 | Kawaguchi |
| 2002/0016548 A1 | 2/2002 | Stadler et al. |
| 2002/0019586 A1 | 2/2002 | Teller et al. |
| 2002/0035337 A1 | 3/2002 | Oka |
| 2002/0082645 A1 | 6/2002 | Sweeney |
| 2002/0107450 A1 | 8/2002 | Ogura |
| 2002/0143262 A1 | 10/2002 | Bardy |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0013974 A1 | 1/2003 | Natarajan et al. |
| 2003/0045805 A1 | 3/2003 | Sheldon et al. |
| 2003/0055352 A1 | 3/2003 | Hayek et al. |
| 2003/0069608 A1 | 4/2003 | Sweeney |
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105496 A1 | 6/2003 | Yu et al. |
| 2003/0120159 A1 | 6/2003 | Mohler |
| 2003/0158492 A1 | 8/2003 | Sheldon et al. |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2003/0233132 A1 | 12/2003 | Pastore et al. |
| 2004/0024423 A1 | 2/2004 | Lincoln et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0073093 A1 | 4/2004 | Hatlestad |
| 2004/0078059 A1 | 4/2004 | Ding et al. |
| 2004/0078060 A1 | 4/2004 | Ding et al. |
| 2004/0106960 A1 | 6/2004 | Siejko et al. |
| 2004/0106961 A1 | 6/2004 | Siejko et al. |
| 2004/0106962 A1 | 6/2004 | Mai et al. |
| 2004/0111040 A1 | 6/2004 | Ni et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0215265 A1 | 10/2004 | Keizer |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0027323 A1 | 2/2005 | Mulligan et al. |
| 2005/0033190 A1 | 2/2005 | Bauer |
| 2005/0060001 A1 | 3/2005 | Singhal et al. |
| 2005/0102001 A1 | 5/2005 | Maile et al. |
| 2005/0148896 A1 | 7/2005 | Siejko et al. |
| 2005/0148897 A1 | 7/2005 | Cho et al. |
| 2005/0149136 A1 | 7/2005 | Siejko et al. |
| 2006/0020295 A1 | 1/2006 | Brockway et al. |
| 2006/0041280 A1 | 2/2006 | Stahmann et al. |
| 2006/0161070 A1 | 7/2006 | Siejko et al. |
| 2006/0270939 A1 | 11/2006 | Wariar et al. |
| 2008/0177191 A1 | 7/2008 | Patangay et al. |

FOREIGN PATENT DOCUMENTS

| | | | |
|---|---|---|---|
| EP | 0709058 | A1 | 1/1996 |
| EP | 0762908 | B1 | 3/1997 |
| JP | 2000-316825 | | 11/2000 |
| WO | WO-0156651 | A1 | 8/2001 |
| WO | WO-2006078757 | A1 | 7/2006 |

| | | |
|---|---|---|
| WO | WO-2006127594 A2 | 11/2006 |
| WO | WO-2006127594 A3 | 11/2006 |

OTHER PUBLICATIONS

Smith, Damon, et al., "Influence of the Aortic Component of the Second Heart Sound on Left Ventricular Maximal Negative dP/dt in the Dog", *Am. J. Cardiol.*, 55: 205, (1985),205-209.

Wariar, R., et al., "Systems and Methods for Multi-Axis Cardiac Vibration Measurements", U.S. Appl. No. 11/135,985, filed May 24, 2004.

Zhang, Y., et al., "Ischemia Detection Using a Heart Sound Sensor", U.S. Appl. No. 11/148,107, filed Jun. 8, 2005, 41 pgs.

"U.S. Appl. No. 11/135,985 Non-Final Office Action Mailed Sep. 25, 2007", 11 Pages.

"International Search Report and Written Opinion for Application No. PCT/US2006/001801, date mailed Jun. 16, 2006", 12 Pages.

Pinchak, Alfred C., et al., "Multiaxial Accelerometers", *Encyclopedia of Medical Devices and Instrumentation*, vol. 1, *Department of Electrical and Computer Engineering*, (1988), 11 Pages.

"U.S. Appl. No. 10/334,694, filed Dec. 3, 2007 to Final Office Action mailed Oct. 1, 2007", 21 pgs.

"U.S. Appl. No. 10/334,694 Non-Final Office Action mailed Mar. 19, 2008", 15 pgs.

"U.S. Appl. No. 11/037,275, Non-Final Office Action mailed Dec. 12, 2007", 17 pgs.

"PCT Application No. PCT/US2007/006345, International Search Report mailed Oct. 24, 2007", 6 pgs.

"PCT Application No. PCT/US2007/006345, Written Opinion mailed Oct. 24, 2007", 8 pgs.

"U.S. Appl. No. 10/334,694, Final Office Action mailed Oct. 7, 2008", 14 pgs.

"U.S. Appl. No. 10/334,694, filed Jun. 19, 2008 to Non-Final Office Action mailed Mar. 19, 2008", 20 pgs.

"U.S. Appl. No. 11/037,275 Final Office Action mailed Jun. 17, 2008", 13 pgs.

"U.S. Appl. No. 11/037,278, filed Sep. 17, 2008 to Final Office Action mailed Jun. 17, 2008", 12 pages.

"U.S. Appl. No. 11/135,985 Notice of Allowance mailed Apr. 25, 2008", 4 pgs.

"U.S. Appl. No. 11/148,107, Examiner Interview Summary mailed Oct. 9, 2008", 4 pgs.

"U.S. Appl. No. 11/148,107, Restriction Requirement mailed May 30, 2008", 6 pgs.

"U.S. Appl. No. 11/148,107, filed Oct. 20, 2008 to Non-Final Office Action mailed Jul. 18, 2008", 9 pgs.

"U.S. Appl. No. 11/148,107, Non-Final Office Action mailed Jul. 18, 2008", 8 pgs.

"U.S. Appl. No. 11/148,107, filed Jun. 30, 2008 to Restriction Requirement mailed May 30, 2008", 7 pgs.

"U.S. Appl. No. 11/275,800, Non-Final Office Action mailed May 2, 2008", 12 pgs.

"U.S. Appl. No. 11/275,800, filed Aug. 29, 2008 to Non-Final Office Action mailed May 2, 2008", 13 pages.

"U.S. Appl. No. 11/277,773, Examiner Interview Summary mailed Oct. 2, 2008", 2 pgs.

"U.S. Appl. No. 11/277,773, Non-Final Office Action mailed Jun. 25, 2008", 16 pgs.

"U.S. Appl. No. 11/277,773, filed Jun. 2, 2008 to Restriction Requirement mailed May 2, 2008", 26 pgs.

"U.S. Appl. No. 11/277,773, filed Oct. 27, 2008 to Office Action mailed Jun. 25, 2008", 15 pages.

DETERMINING A PATIENT'S POSTURE FROM MECHANICAL VIBRATIONS OF THE HEART

CROSS-REFERENCE TO RELATED APPLICATION

This application is related to co-pending, commonly assigned U.S. patent application Ser. No. 10/703,175, entitled "A DUAL USE SENSOR FOR RATE RESPONSIVE PACING AND HEART SOUND MONITORING," filed on Nov. 6, 2003, and U.S. patent application Ser. No. 10/334,694 entitled "METHOD AND APPARATUS FOR MONITORING OF DIASTOLIC HEMODYNAMICS," filed on Dec. 30, 2002, which are hereby incorporated by reference.

TECHNICAL FIELD

The field generally relates to implantable medical devices and, in particular, but not by way of limitation, to systems and methods for determining a patient's posture by monitoring the mechanical functions of the heart.

BACKGROUND

Implantable medical devices (IMDs) are devices designed to be implanted into a patient. Some examples of these devices include cardiac rhythm management (CRM) devices such as implantable pacemakers and implantable cardioverter defibrillators (ICDs). The devices are used to treat patients using electrical therapy and to aid a physician or caregiver in patient diagnosis through internal monitoring of a patient's condition. Implantable devices may also include electrical leads that are either separate from, or connected to, a CRM. Electrical leads connected to CRM devices are located in or near a heart to provide electrical therapy to the heart. The electrical leads are also in communication with sense amplifiers of the CRM devices to monitor electrical heart activity within a patient. Other examples of implantable medical devices include implantable insulin pumps or devices implanted to administer drugs to a patient.

Congestive heart failure is a disease that causes the ventricles of the heart to have a reduced ability to contract which results in an inadequate amount of blood being pumped into circulation. Because blood is being pumped away from the lungs at a reduced rate, fluid may build up in a patient's lungs and cause difficulty in breathing. As a patient's condition worsens, the patient may develop a tendency to rest in an elevated posture to reduce the fluid buildup in his or her lungs. Some CRM devices provide electrical therapy to treat congestive heart failure. The present inventors have recognized a need for improved monitoring of the condition of a congestive heart failure patient.

SUMMARY

Systems and methods are provided for determining a patient's posture by monitoring heart sounds. In one system example, the system comprises an implantable medical device that includes a sensor operable to produce an electrical signal representative of heart sounds, a sensor interface circuit coupled to the sensor to produce a heart sound signal, and a controller circuit coupled to the sensor interface circuit. The heart sounds are associated with mechanical activity of a patient's heart and the controller circuit is operable to detect a posture of the patient from a heart sound signal.

In one method example, the method comprises sensing heart sounds associated with activity of a patient's heart using an implantable medical device and determining posture information of the patient from the heart sounds.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

The present application discusses, among other things, systems and methods for determining a patient's posture by monitoring heart sounds. Implantable medical devices (IMDs) may include sensors to monitor internal patient parameters. For example, an acoustic sensor can be used to sense heart sounds. Heart sounds are the sounds resulting from the physical contractions of the heart. Heart sound one (S1) occurs when a heart's ventricles receive blood from the atria. S1 is the sound made by the heart during the near simultaneous closure of the mitral and tricuspid valves. Heart sound two (S2) occurs when the ventricles are emptied. S2 is the sound made by the heart during the near simultaneous closure of the aortic and pulmonic valves. When a person is standing or sitting, the amplitude of the heart sounds and the frequency components of the heart sounds of the person are different than when the person is lying down. By monitoring the amplitude or the frequency spectrum of the heart sounds it can be determined whether the patient is laying down or is in an upright position.

Figure 1:
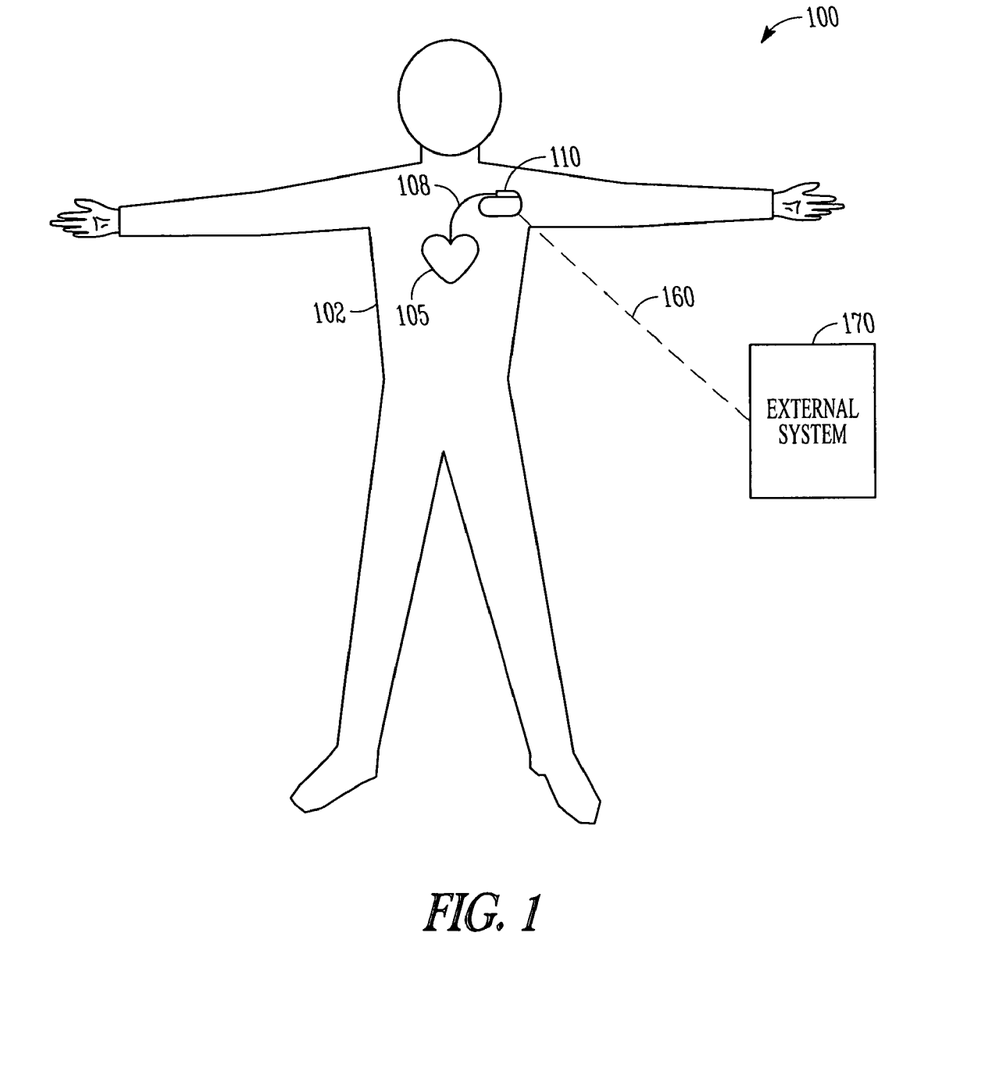
FIG. 1 illustrates an embodiment of a system that uses an implantable medical device.

FIG. 1 illustrates an embodiment of a system 100 that uses an IMD 110. The system 100 shown is one embodiment of portions of a system 100 used to treat a cardiac arrhythmia. A pulse generator (PG) or other IMD 110 is coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also includes an IMD programmer or other external system 170 that provides wireless communication signals 160 to communicate with the MD 110, such as by using telemetry or radio frequency (RF) signals.

Cardiac lead 108 includes a proximal end that is coupled to IMD 110 and a distal end, coupled by an electrode or electrodes to one or more portions of a heart 105. The electrodes are for delivering atrial and/or ventricular cardioversion/defibrillation and/or pacing or resynchronization therapy to the heart 105. IMD 110 includes components that are enclosed in a hermetically-sealed canister or "can." Additional electrodes may be located on the can, or on an insulating header, or on other portions of IMD 110, for providing unipolar pacing and/or defibrillation energy in conjunction with the electrodes disposed on or around heart 105. The lead 108 or leads and electrodes are also used for sensing electrical activity of a heart 105.

Figure 2:
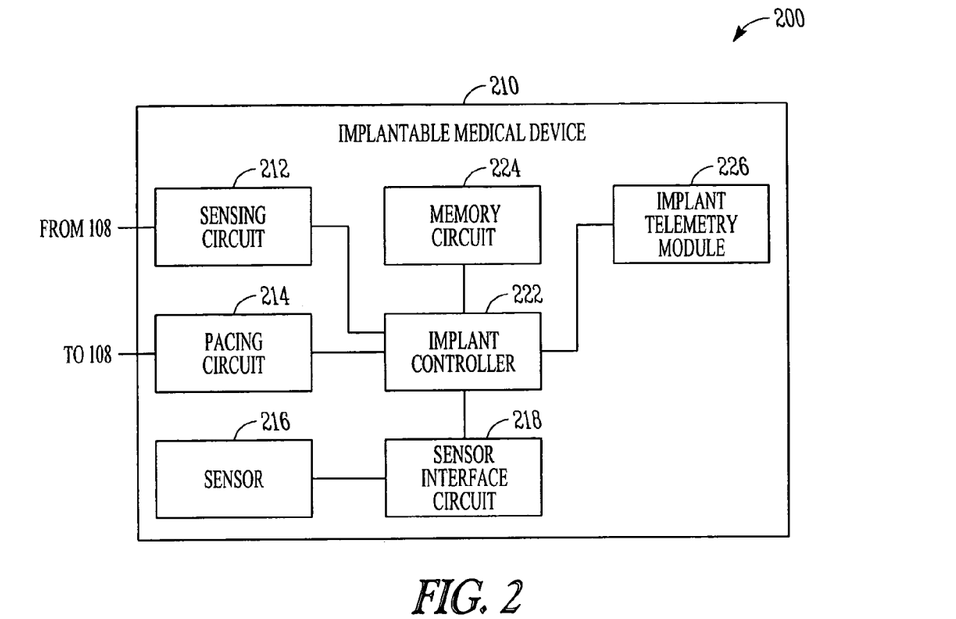
FIG. 2 is a block diagram of an implantable medical device.

FIG. 2 is a block diagram 200 of an embodiment of an implantable medical device (IMD) 210 used in a system for cardiac rhythm management. The IMD 210 includes a signal sensing circuit 212 to sense electrical signals on the lead or leads 108 and electrodes. To sense the electrical signals, the sensing circuit 212 includes sense amplifier circuits (not shown). The IMD 210 includes a pacing circuit 214 to deliver electrical therapy to a heart through the lead or leads 108 and electrodes. The electrical therapy includes altering a heart rate through electrical stimulation as well as re-synchronizing the depolarizations of heart chambers without necessarily altering a heart rate. Sensor 216 is operable to produce an electrical signal representative of heart sounds. In one embodiment, the sensor 216 is an accelerometer that senses vibrations associated with mechanical activity of a heart. The IMD 210 also includes a controller circuit 222 and memory circuit 224. Sensor interface circuit 218 is coupled to the sensor 216 and processes the sensor signal to produce a heart sound signal readable by controller circuit 222. The controller circuit 222 is operable to detect a posture of the patient from the heart sound signal, such as by executing an algorithm or algorithms implemented by hardware, software, firmware or any combination of hardware, software or firmware.

In some embodiments, the controller circuit 222 is operable to detect a posture of the patient from a frequency spectrum of the heart sound signal. The spectral energy of the S1 and S2 heart sounds are generally within a range of about 10 Hz to about 100 Hz. When a person changes from an upright position to a supine position, the spectral energy rolls off at a lower frequency, i.e. more high frequency components are attenuated. When a person changes from a supine to an upright position, more high frequency components appear. In one such embodiment, the controller circuit 222 is operable to perform a spectral analysis of energy of the heart sound signals to detect this change in the frequency spectrum of a patient. In another embodiment, the spectral analysis to detect the change in frequency includes a fast Fourier transform.

To detect a change in the frequency spectrum of the heart sound signal, in one embodiment the memory circuit 224 is operable to store a baseline frequency spectrum for the patient requiring the IMD 210. The baseline can be either for the upright or supine position. The controller circuit 222 then detects a change in the position by a comparison of the baseline frequency spectrum to the current frequency spectrum. The change can be either the addition of higher frequencies to a supine baseline or the subtraction of the higher frequencies from an upright baseline. In one embodiment, the baseline frequency spectrum is obtained from a personal profile of the patient. In another embodiment, the baseline frequency spectrum is obtained from a patient population.

Figure 3:
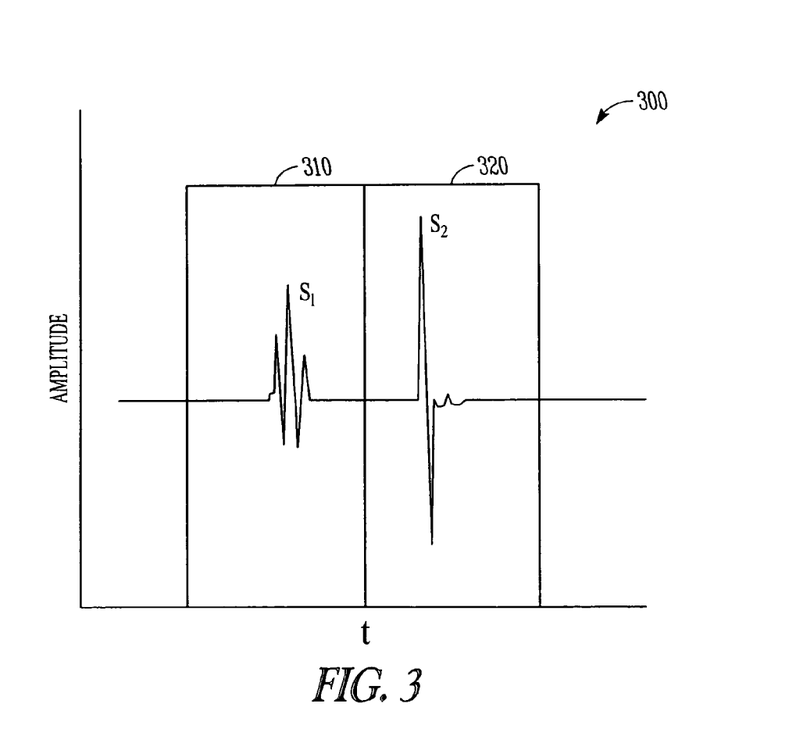
FIG. 3 is a graphical representation of S1 and S2 heart sound signals as a function of time.

In other embodiments, the controller circuit 222 is operable to detect a posture of the patient from an amplitude or magnitude of the heart sound signal. When a person is in a supine position, the S1 and S2 heart sounds are significantly smaller in amplitude than when the person is standing or sitting. FIG. 3 shows a graphical representation 300 of amplitudes of S1 and S2 heart sound signals as a function of time. The graph shows the time relationship between the heart sounds. To measure the heart sounds an S1 timing window 310 is begun to measure the S1 signal. The S1 window 310 is timed in relation to a ventricular event (not shown). After the S1 window expires an S2 timing window 320 is begun to measure the S2 heart sounds. In one embodiment, the S1 and S2 timing windows are taken or determined specifically for one patient. In another embodiment, the S1 and S2 timing windows are determined from a patient population.

Returning to FIG. 2, sensor interface circuit 218 provides a heart signal amplitude value to the controller circuit 222. In one embodiment, the controller circuit determines the posture of a patient from the amplitude value. In another embodiment, the IMD 210 detects a change in amplitude of the heart sound signal. In the embodiment, the memory circuit 224 is operable to store a baseline amplitude value that can be either for the upright or supine position. The controller circuit 222 then detects a change in the position by a comparison of the baseline amplitude to the current measured amplitude to determine a patient position from the change from the baseline amplitude. The comparison may involve a single maximum value, a central tendency maximum value such as a mean maximum value, or a morphology comparison.

In yet another embodiment, the presence of the higher frequencies or higher amplitudes is given a logical state by the controller circuit 222, such as a logical "1," denoting that the higher frequencies or higher amplitudes are present and the person is upright. A logical "0" indicates that the higher frequencies or higher amplitudes are not present and the person is lying down. In yet another embodiment, the controller circuit 222 is operable to apply a weighing or scoring over a plurality of cardiac cycles before deeming that the patient is standing or supine. Such a scoring or weighing is useful to accommodate gradual changes in posture.

Figure 4:
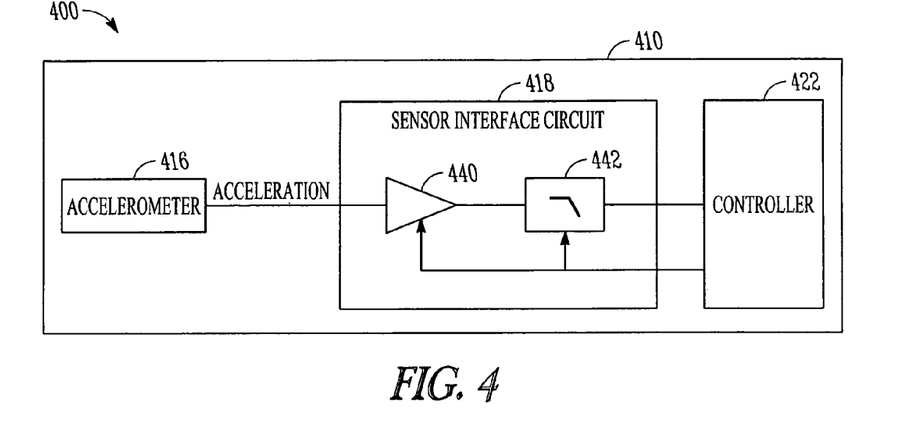
FIG. 4 is a block diagram of another embodiment of an implantable medical device.

FIG. 4 is a block diagram 400 of another embodiment of an IMD 410. In the embodiment, the sensor 416 is an accelerometer and provides electrical signals representative of acceleration to the sensor processing circuit 418. The accelerometer detects mechanical vibrations of the heart that correspond to the S1 and S2 heart sounds. The sensor interface circuit 418 includes amplifier circuit 440 and low-pass filter circuit 442. The sensor interface circuit 418 provides a heart sound signal to controller circuit 422. The controller circuit 422 then detects a posture of the patient from the frequency spectrum or the amplitude of the heart sound signal. The controller circuit is operable to adjust the parameters of the amplifier circuit 440 and filter circuit 442. For example, in one embodiment, the amplifier circuit 440 provides a signal gain of one thousand. In another example, the controller circuit 422 adjusts the filter circuit 442 to single pole roll-off.

Figure 5:
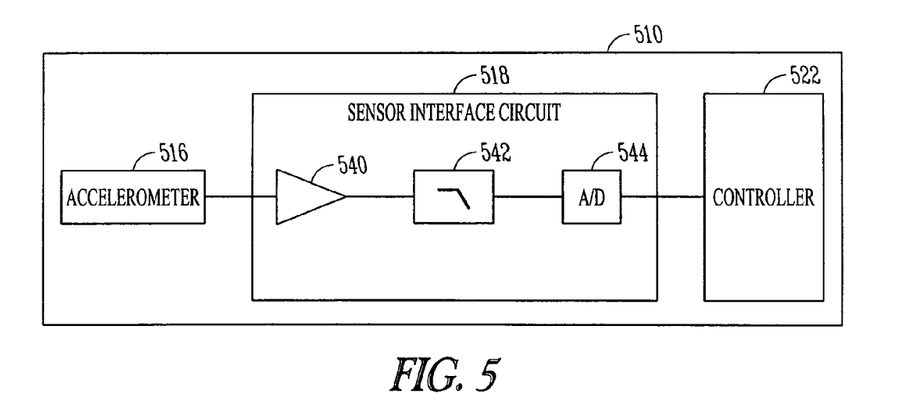
FIG. 5 is a block diagram of another embodiment of an implantable medical device.

FIG. 5 is a block diagram of an IMD 510 that includes another embodiment of a sensor interface circuit 518. In addition to amplifier 540 and low pass filter 542, the embodiment includes an analog-to-digital converter circuit 544 to convert the heart sound signals from accelerometer 516 into digital values. The controller circuit 522 then determines a maximum value or values of the heart sound signal values and compares the maximum to a previously stored maximum or baseline to determine a posture of the patient.

Figure 6:
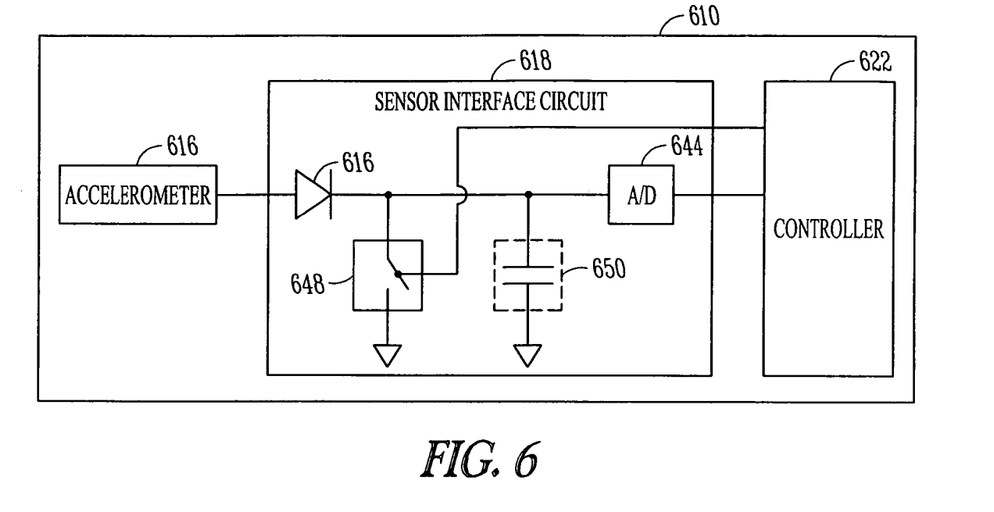
FIG. 6 is a block diagram of another embodiment of an implantable medical device.

Further embodiments of a sensor interface circuit used when monitoring the amplitude or magnitude of a heart sound signal include peak detector circuits and level detector circuits. FIG. 6 is a block diagram of an example of an IMD 610 where the sensor interface circuit 618 includes a peak detector circuit. The sensor shown is an accelerometer 616. The peak detector circuit includes a diode 646, capacitor 650 and switch 648. The peak detector circuit stores the peak value of a heart sound signal detected during the timing window onto capacitor 650. This peak amplitude value is converted to a digital value by analog-to-digital converter 644. The sampling rate of the analog-to-digital converter is controlled by the controller circuit 622. The digital value is then used to determine a posture of a patient by any of the methods discussed above.

Returning to FIG. 2, another embodiment of the IMD 210 includes a tilt sensor coupled to the controller circuit 222 in addition to the heart sound sensor 216. A tilt sensor measures DC acceleration in each of three main axes and provides electrical signals related to this acceleration. The tilt sensor signals are useful in deducing patient posture. However, deducing a patient's posture from the tilt sensor signals is complicated by not always knowing the orientation of an IMD in a patient. In this embodiment, the controller circuit 222 is operable to determine the posture of the patient by correlating the heart sound signals and the tilt sensor signals.

Determining a patient's posture is useful in treating patients suffering from congestive heart failure or in detecting that a patient is suffering from congestive heart failure. As discussed previously some cardiac rhythm management (CRM) devices provide electrical pacing therapy to both ventricles of a patient's heart to improve the efficacy of contractions of the ventricles. Knowing a patient's posture at rest may give an indication of the efficacy of the pacing therapy. For example, information that the patient is resting for extended periods in an increasingly upright position may indicate that the patient's condition is worsening. In addition, if the patient is not being treated for congestive heart failure it may be an indication that the patient is developing congestive heart failure. Thus combining a patient's posture with activity level provides useful information. In one embodiment, a patient's activity level is deduced using time of day. If a patient is an upright position during nighttime hours, it may indicate that the patient is sleeping in an upright position to ease his or her breathing. In one embodiment, the controller circuit 222 is operable to provide a congestive heart failure status indicator as a result of trending this information over time.

Sensors have been included in CRM devices to monitor a patient's activity. Indications of a patient's activity level are used to adjust a rate of pacing therapy of a CRM device. Generally, these CRM devices increase a pacing rate according to an algorithm based on the activity level of the patient indicated by the sensor. This is sometimes referred to as rate responsive pacing. An accelerometer is one type of sensor 216 that provides electrical signals representative of patient activity. If an accelerometer is also used to monitor heart sounds, the heart sound signals should be measured while the patient is at rest. Determining that a patient is at rest can be deduced from a patient's heart rate if the IMD 210 includes rate responsive pacing therapy—i.e. the patient's heart rate is at the resting heart rate.

In one embodiment, the IMD 210 includes a sensor to monitor patient activity and a sensor 216 to monitor heart sounds. In another embodiment, the sensor 216 is operable to produce electrical signals representative of both heart sounds and patient activity. A discussion of using a sensor to monitor both patient physical activity and heart sounds is found in the previously mentioned U.S. patent application Ser. No. 10/703,175, entitled "A DUAL USE SENSOR FOR RATE RESPONSIVE PACING AND HEART SOUND MONITORING," now U.S. Pat. No. 7,248,923, which is incorporated herein by reference.

In yet other embodiments, information from posture at rest can also be combined with other sensor information to detect congestive heart failure. In one embodiment, the system to determine a patient's posture by monitoring heart sounds further includes a pressure sensor coupled to the IMD 210. The pressure sensor is located and operable to produce electrical signals related to thoracic pressure of a patient. An increase in thoracic pressure may indicate fluid buildup in a patient's lungs. The controller circuit 222 is operable to use both posture information and the pressure information to provide a congestive heart failure status indicator.

In another embodiment, the system further includes a transthoracic impedance measurement circuit coupled to the IMD 210. The transthoracic impedance measurement circuit is operable to measure impedance across a thorax of the patient. A decrease in thoracic impedance may indicate fluid buildup in a patient's lungs. In the embodiment, the controller circuit 222 is operable to use posture information and transthoracic impedance information to provide a congestive heart failure status indicator.

Other embodiments of a system to determine a patient's posture by monitoring heart sounds include an external device operable to communicate with the IMD 210. The IMD 210 includes a communication module, such as telemetry module 226, to transmit or receive information from the external device using wireless communication signals. In one embodiment, the external device includes a display to display patient posture information obtained using the heart sound signal. In another embodiment, the display of patient posture information includes a histogram of patient posture. In yet another embodiment, the display of patient posture information includes trending information of patient posture. For example, the trending information may include information that the patient is resting for extended periods in an upright condition. In some embodiments, the controller circuit 222 processes the heart sound information and transmits posture information to the external device. In other embodiments, the controller circuit 222 transmits heart sound information to the external device and the external device derives the posture information. In yet another embodiment, the external device is operable to communicate with a computer network such as, for example, a hospital network or global computer network such as the internet.

Figure 7:
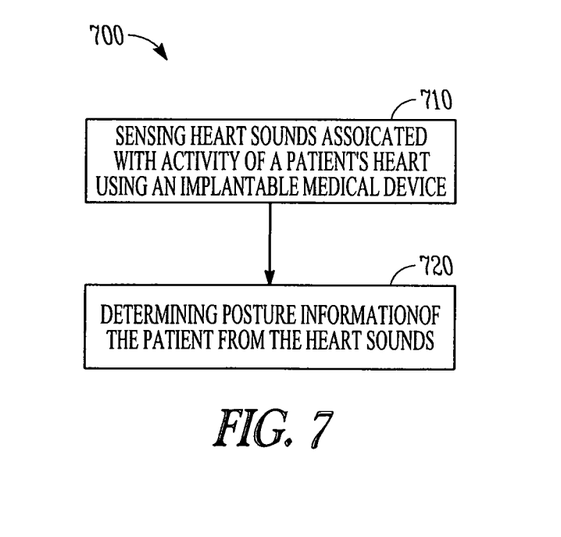
FIG. 7 is a block diagram of a method for determining posture of a patient.

FIG. 7 is a block diagram 700 of a method for determining posture of a patient. At 710, heart sounds associated with activity of a patient's heart are sensed using an implantable medical device. At 720, posture information of the patient is determined from the heart sounds. In one embodiment, the posture information is determined using a frequency spectrum of the heart sounds. In another embodiment, the posture information is determined using a magnitude of the heart sounds.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A system comprising:
    an implantable medical device comprising:
        a sensor operable to produce an electrical signal representative of heart sounds, the heart sounds associated with mechanical activity of a patient's heart;
        a sensor interface circuit coupled to the sensor to produce a heart sound signal; and
        a controller circuit, coupled to the sensor interface circuit, wherein the controller circuit is operable to:
    discriminate a posture of the patient from among a plurality of postures using the heart sound signal; and
    provide an indication of the patient posture to user or process.

2. The system of claim 1, wherein the controller circuit is operable to detect a posture of the patient from change in a frequency spectrum of the heart sound signal.

3. The system of claim 2, wherein the controller circuit is operable to perform a spectral analysis of energy of the heart sound signals to detect the change in the frequency spectrum.

4. The system of claim 3, wherein the spectral analysis includes a fast Fourier transform.

5. The system of claim 1, wherein the controller circuit is operable to detect a posture of the patient from an amplitude of the heart sound signal.

6. The system of claim 5, wherein the sensor interface circuit includes a peak detector circuit, and wherein the controller circuit detects a posture of the patient by detecting a change in amplitude of the heart sound signals using an output of the peak detector circuit.

7. The system of claim 5, wherein the sensor interface circuit includes an analog-to-digital converter to convert the heart sound signal into digital values, and wherein the controller detects a posture of the patient from a change in amplitude of the heart sound signal, and wherein the change in amplitude is determined using the digital values.

8. The system of claim 7, wherein the implantable medical device further includes a memory and the digital values are stored in the memory.

9. The system of claim 1, wherein the implantable medical device further includes a tilt sensor coupled to the controller, the tilt sensor operable to produce an electrical signal related to a patient posture, and wherein the controller circuit is operable to detect the posture of the patient from both the heart sound signal and the tilt sensor signal.

10. The system of claim 1, wherein the sensor is operable to produce electrical signals representative of both heart sounds and patient activity.

11. The system of claim 1, wherein the system further includes a pressure sensor coupled to the implantable medical device, wherein the pressure sensor is operable to produce electrical signals related to thoracic pressure of a patient, and wherein the controller circuit is operable to use both posture information and pressure information to provide a congestive heart failure status indicator.

12. The system of claim 1, wherein the system further includes a transthoracic impedance measurement circuit coupled to the implantable medical device, wherein the transthoracic impedance measurement circuit is operable to measure impedance across a thorax of the patient, and wherein the controller circuit uses posture information and transthoracic impedance information to provide a congestive heart failure status indicator.

13. The system of claim 1, wherein the implantable medical device includes a cardiac rhythm management device.

14. The system of claim 1, wherein the system further includes an external device operable to communicate with the implantable device, wherein the external device includes a display, and wherein the external device is further operable to display patient posture information obtained from the heart sound signal.

15. The system of claim 14, wherein the patient posture information includes a histogram of patient posture.

16. The system of claim 14, wherein the patient posture information includes trending information of patient posture.

17. The system of claim 14, wherein the external device is operable to communicate with a computer network.

18. A system comprising:
    a sensor operable to produce an electrical heart sound signal representative of heart sounds associated with mechanical activity of a patient's heart; and
    a controller circuit configured to:
        determine a change from a baseline for the heart sound signal;
        discriminate a posture of the patient from among a plurality of postures using the change from the baseline of the heart sound signal; and provide an indication of the patient posture to a user or process.

19. The system of claim 18, wherein the change from the baseline is a change in amplitude of the heart sound signal.

20. The system of claim 18, wherein the change from the baseline is a change in a frequency spectrum of the heart sound signal.

* * * * *